(12) United States Patent
Brill et al.

(10) Patent No.: US 8,658,982 B2
(45) Date of Patent: Feb. 25, 2014

(54) OPTICAL METHOD AND SYSTEM UTILIZING OPERATING WITH DEEP OR VACUUM UV SPECTRA

(75) Inventors: Boaz Brill, Rehovoth (IL); Oleg Korshunov, Rehovot (IL)

(73) Assignee: Nova Measuring Instruments Ltd., Rehovet (IL)

( * ) Notice: Subject to any disclaimer, the term of this patent is extended or adjusted under 35 U.S.C. 154(b) by 762 days.

(21) Appl. No.: 12/663,165

(22) PCT Filed: Jun. 5, 2008

(86) PCT No.: PCT/IL2008/000780
§ 371 (c)(1),
(2), (4) Date: Dec. 4, 2009

(87) PCT Pub. No.: WO2008/149373
PCT Pub. Date: Dec. 11, 2008

(65) Prior Publication Data
US 2010/0181490 A1    Jul. 22, 2010

(30) Foreign Application Priority Data
Jun. 5, 2007    (IL) .......................................... 183693

(51) Int. Cl.
G01N 21/15    (2006.01)
(52) U.S. Cl.
USPC ........................................................ 250/372
(58) Field of Classification Search
USPC ........................................................ 250/372
See application file for complete search history.

(56) References Cited

U.S. PATENT DOCUMENTS

| 6,523,572 | B1 | 2/2003 | Levin et al. |
| 7,067,818 | B2 | 6/2006 | Harrison |
| 7,096,752 | B1 | 8/2006 | Lehman |
| 2002/0149774 | A1* | 10/2002 | McAninch ..................... 356/445 |
| 2002/0191166 | A1 | 12/2002 | Hasegawa et al. |
| 2004/0156049 | A1 | 8/2004 | Breninger et al. |
| 2005/0077474 | A1 | 4/2005 | Finarov |
| 2006/0146300 | A1 | 7/2006 | Simon et al. |

FOREIGN PATENT DOCUMENTS

JP    A-2005-64210    3/2005

OTHER PUBLICATIONS

International Search Report mailed on Jan. 23, 2009 in corresponding International Application No. PCT/IL2008/000780.

* cited by examiner

*Primary Examiner* — David Porta
*Assistant Examiner* — Shun Lee
(74) *Attorney, Agent, or Firm* — The Law Office of Michael E. Kondoudis

(57) ABSTRACT

An apparatus and method are presented for use in optical processing of an article. The apparatus comprises: one or more optical windows for directing predetermined electromagnetic radiation therethrough to illuminate a region of interest and collecting radiation returned from the illuminated region; and two or more ports operable for inputting or discharging one or more gases from the vicinity of the region of interest on the article being processed to create in the vicinity of said region a substantially static state of environment, non-absorbable for said electromagnetic radiation, thereby reducing amount of ambient gas in the vicinity of said region of interest and enabling optical processing of the article while maintaining it in the ambient gas environment.

15 Claims, 6 Drawing Sheets

OPTICAL METHOD AND SYSTEM UTILIZING OPERATING WITH DEEP OR VACUUM UV SPECTRA

FIELD OF THE INVENTION

This invention is generally in the field of optical inspection, monitoring, or imaging techniques, and relates to an optical system and method operable with Deep and Vacuum UV spectra.

BACKGROUND OF THE INVENTION

There are many applications in different fields using radiation of different electromagnetic spectral ranges for various purposes. Such purposes could include, but not limited to for example, writing patterns on a substrate, inspecting a surface, performing measurements and others. Relevant spectral ranges of the electromagnetic radiation may include visible light, IR, UV and X-ray radiation. Operation with radiation of some spectral ranges in many cases suffers from interaction of light with a medium through which the light beam has to propagate (e.g. air in case of Deep and Vacuum UV and X-ray). Such interaction may include different effects, such as absorption, scattering (elastic or inelastic), all resulting in that a part of the light beam intensity is lost on the beam's way to an addressed position. Accordingly, the power on the interaction spot at said addressed position is smaller than desired and at the same time unwanted secondary effects might occur (e.g. background signal, spot widening etc.).

In most applications of the kind specified the medium in the optical path of the beam is air. Air is known to transmit well in several "atmospheric windows", such as the optical window between ~190-1400 nm, including the visible part of the spectrum, the near IR and parts of the UV, the mid-IR window around ~3.5-5 microns and the far-IR window around ~8-12 microns. The atmospheric windows are defined such that the overall absorption of all gasses found in the atmosphere is low. Outside these windows specific gasses, e.g. such as Oxygen (blocking transmission below 190 nm), water vaporand Carbon dioxide have absorption bands that limit the transmission in atmosphere.

US 2005/077474, assigned to the assignee of the present application, describes optical method and system for use in processing articles by VUV radiation. This technique utilizes localizing incident VUV radiation propagation from an optical head assembly towards a processing site on the article outside the optical head assembly and localizing reflected VUV radiation propagation from said processing site towards the optical head assembly, by localizing a medium, non-absorbing with respect to VUV radiation, in within the light propagation path in the vicinity of said site outside the optical head assembly.

General Description

The present invention provides a novel apparatus and method enabling optical processing of an article while in a free space (air environment), eliminating a need for maintaining the article in a vacuum chamber during the processing. It should be understood that optical processing refers to any one of inspection, examination, monitoring, measurement, exposure and the like procedure applied to an article by irradiating it by electromagnetic radiation and detecting and analyzing the article response to said radiation.

The invention provides for localizing a radiation spot on the surface of an article, by creating specific local conditions in the vicinity of a processing site on the article's surface being irradiated (preferably around the intended interaction spot), such that the interaction of an optical beam with atmosphere in the vicinity of the processing site is reduced to an acceptable level, while keeping the article in air environment. The local condition in the vicinity of the processing site is a condition of minimized amount of ambient gases (typically air) in the vicinity of the processing site. This is achieved by creating, in the vicinity of region of interest (i.e. vicinity of the processing site), substantially static (or quasi-static) state of environment, non-absorbable for said spectral range or wavelength.

According to some embodiments of the invention, the above-described local conditions around a processing site (measurement spot) are created using injection of gas non absorbing for a spectrum used (inert gas), such that other gasses from the surrounding atmosphere are pushed out to a level that their interaction with optical beams are no longer significant. In this respect, an inert gas is any gas, which does not have a substantial absorption in the intended part of the spectrum. For the example of VUV, Nitrogen or Argon could be used to allow transmission below 190 nm where atmospheric Oxygen ($O_2$) is absorbing. For the case of an X-ray beam, Helium could be used as the inert gas since its interaction with the radiation is minimal due to its low atomic number.

According to some other embodiments of the invention, the above-defined static state conditions are created by discharging (pumping) ambient gas(es) from the vicinity of the region of interest.

There is thus provided, according to one broad aspect of the invention, an apparatus for use in optical processing of an article, the apparatus comprising: one or more optical windows for directing predetermined electromagnetic radiation therethrough to illuminate a region of interest and collecting radiation returned from the illuminated region; and two or more ports operable for inputting or discharging one or more gases from the vicinity of the region of interest on the article being processed to create in the vicinity of said region a substantially static state of environment non-absorbable for said electromagnetic radiation, thereby reducing amount of ambient gas in the vicinity of said region of interest and enabling optical processing of the article while maintaining it in the ambient gas environment.

According to some embodiments of the invention, the apparatus comprises a facet having a substantially planar surface formed with one or more optical windows. Inert gas (non-absorbing for radiation being used) is supplied into a gap between the planar surface carrying the optical window (s). The inert gas is supplied in two (or more) opposite gas jets which interfere (meet) at the gap region below the optical window(s), i.e. in the vicinity of the processing site, resulting in a zone of substantially increased gas pressure in the vicinity of the processing site.

Thus, the facet of the apparatus in which the planar surface with the optical window(s) is formed has at least two orifices for flowing gas therethrough into said gap between the optical window(s) and the article. The arrangement of the optical window(s) and gas inlet orifice(s) is such that the gas flow in said gap is substantially parallel to said planar surface.

The gas flowing through the gap may be discharged via at least one outlet orifice made in said facet.

The arrangement of optical window(s) and said inlet orifice (s) may be such that the gas flows through the gap and is discharged therefrom while in a substantially laminar flow.

The arrangement of the optical window(s) and the inlet orifice(s) and outlet orifice(s) made in said facet may be such that a saddle point of the gas flow is provided in the vicinity of the processing site. By this, a zone of relatively high pressure at the saddle point is provided. As indicated above, this can be achieved by arranging the inlet and outlet orifices such that the gas flow comprises gas jets flowing in opposite directions and interfering at said saddle point. In some embodiments, there are at least two inlet and at least two outlet orifices. The outlet orifices may be arranged substantially symmetrically with respect to said saddle point. Similarly, the inlet orifices are arranged substantially symmetrically with respect to said saddle point.

As indicated above, the local conditions of low pressure or vacuum around the intended interaction spot could be created in a dynamic situation without fully evacuating the atmosphere around the whole article. This can be implemented by providing in said facet an array of spaced apart outlet orifices arranged around the optical window and operating for pumping ambient gas out of the gap between the optical window and the article, to thereby provide a zone of relatively low pressure at the vicinity of said processing site.

The outlet orifices may be arranged substantially symmetrically with respect to the optical window. At least some of the orifices are preferably arranged along one or more concentric closed-loop paths centered about said optical window.

In all the above-described embodiments, (injection or vacuum), a distance between the optical window to the article is preferably minimized in order to minimize the interaction path length between the beam and the atmosphere. This can be achieved by allowing movement of the planar surface carrying the optical window along an axis perpendicular to said planar surface. To this end, a flexure associated with the planar surface can be used, being configured and operable to enable said movement of the optical window along.

According to another broad aspect of the invention, there is provided an apparatus for use in optical processing of an article, the apparatus comprising: one or more optical windows for directing predetermined electromagnetic radiation therethrough towards a region of interest and collecting light returned from the illuminated region; and two or more ports for inputting gas, non-absorbable for said radiation towards the region of interest on the article being processed, thereby enabling creation of a substantially static state of environment non-absorbable for said radiation in the vicinity of said region of interest thus reducing amount of ambient gas in the vicinity of said region of interest and enabling optical processing of the article while maintaining it in the ambient gas environment.

In yet another broad aspect of the invention, there is provided an apparatus for use in optical processing of an article, the apparatus comprising: one or more optical windows for directing predetermined electromagnetic radiation therethrough towards a region of interest and collecting light returned from the illuminated region; and two or more ports for discharging ambient gas from the vicinity of the region of interest on the article being processed, thereby enabling creation of a substantially static state of environment non-absorbable for said radiation in the vicinity of said region of interest thus reducing amount of the ambient gas in said region of interest and enabling optical processing of the article while maintaining it in the ambient gas environment.

According to yet further aspect of the invention, there is provided an apparatus for use in optical processing of an article, the apparatus comprising: one or more optical windows for directing predetermined electromagnetic radiation therethrough towards a region of interest and collecting light returned from the illuminated region; and one or more ports operable for inputting or discharging gas from the vicinity of the region of interest on the article being processed, said one or more optical windows being mounted for controllable movement along an axis substantially perpendicular to a plane defined by the optical window.

The invention also provides a method for use in optical processing of an article, the method comprising maintaining an article under processing in ambient gas environment while creating local environmental conditions in a vicinity of a processing site of the article, said local conditions being characterized by substantially static state of environment, non-absorbable for predetermined electromagnetic radiation, in the vicinity of said processing site.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EXEMPLARY EMBODIMENTS

As indicated above, it is often a case that an article is to be processed (monitored, inspected or the like) by light of a spectrum absorbable by ambient medium (air environment). In order to avoid inconveniency associated with maintaining the article in a vacuum chamber during the processing, appropriate environmental conditions in the vicinity of the article under processing, while in air environment, can be provided.

The present invention can generally be used with processing of articles of any type. More specifically, the invention is used for electromagnetic measurements of semiconductor wafers, where the intent is to perform a measurement in the spectral range characterized by wavelength below 190 nm, generally know as Vacuum UV (VUV). An alternative situation is the measurement of a semiconductor wafer using X-ray radiation that is strongly scattered by air.

Figure 1A:
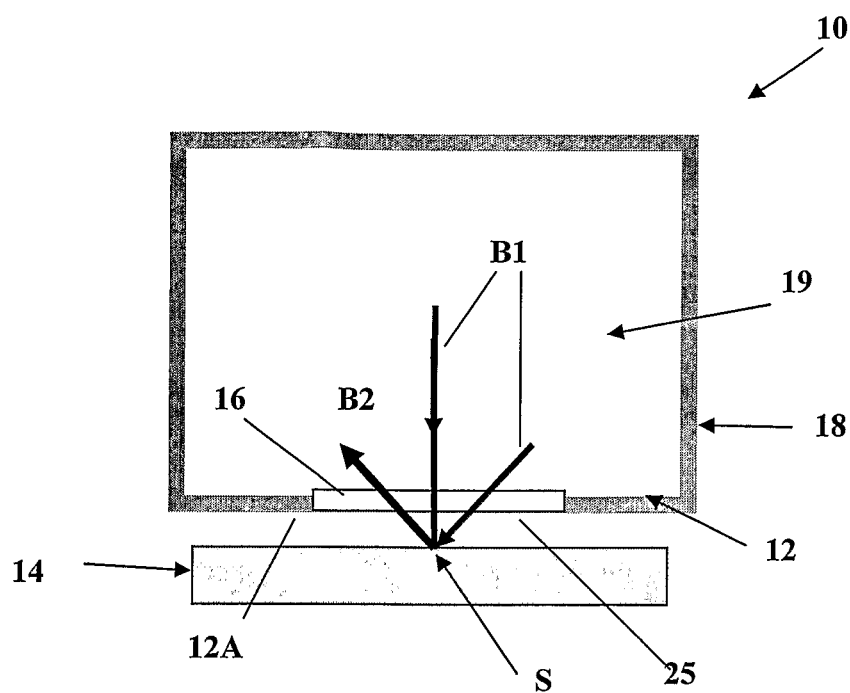
FIGS. 1A and 1B schematically illustrate the principles of light propagation scheme used in the present invention, according to two examples, respectively.
Figure 1B:
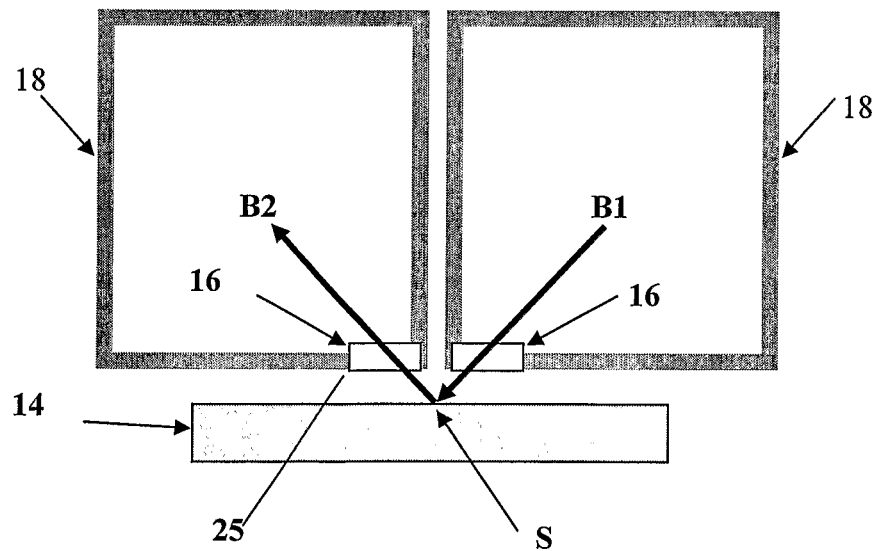

Reference is made to FIGS. 1A and 1B exemplifying an optical window containing part of an apparatus of the present invention. Apparatus, generally designated 10, includes a facet 12, by which the apparatus faces a wafer 14 (constituting an article) being site-by-site processed. Facet 12 has a substantially planar surface thereof at least within a portion 12A of the facet aligned with a processing site S of the wafer. This substantially planar surface 12A is formed with one or more optical windows for transmitting and/or receiving therethrough electromagnetic radiation towards and/or from the processing site S.

The facet 12 is typically a facet of a housing 18 containing an optical system 19 to be applied to the article through the optical window(s). The configuration and operation of the optical system do not form part of the present invention, and therefore need not be described in details, except to note the following: The optical system is adapted for directing an optical beam B1 from a light source unit (not shown) towards the processing site S and detecting (by alight detection unit which is not specifically shown) light response B2 (e.g. reflection) of the illuminated site. The light source as well as the detector may and may not be located inside the housing. For example, the light source and/or detector may be located outside the housing and the latter may contain/define a light propagation path towards and away from the article. It should be noted, although not specifically shown, that an appropriate control system (typically a computer system) is connectable to the output of the detector for analyzing measured data.

In the example of FIG. 1A, the housing 18 and accordingly the optical window 16 is a single-part unit: the incident and returned light beams propagate through the same optical window and the same cavity of the housing. In the example of FIG. 1B, the housing 18 and the optical window 16 is a two-part unit, thus defining two light propagation cavities: one for the incident light propagation and the other for the returned light propagation.

Thus, the apparatus includes optical window(s) which may be associated with the optical system containing housing. The optical window(s) 16 carrying surface 12A is intended to be placed above the article with a gap (volume) 25 between the window(s) 16 and the article 14. The internal part of the optical system (housing) is either evacuated of air or is purged using an inert gas. This situation is mostly static in nature since any changes that may occur in the optical system are internal to this volume. As for the gap between the window and the article it is treated in a different approach (as will be described below) in order to allow easy motion of the article under the window or replacement of the article.

As illustrated in FIGS. 1A and 1B one or more beams B1 designed to interact with the processing site of the article in a limited area referred to as "optical spot" propagate through the optical window(s). Secondary beam(s) B2 is/are created in response to the interaction of the incident beam(s) B1 and the article and travel(s) back to the optical system through the window 16. In the example of FIG. 1B, the optical window is a two-part unit associated with "source module" and "detector module". It should be noted that selection of material(s) from which the optical window is made depends on the spectral range utilized. For example, for the Vacuum UV range materials such as Quartz or MgF can be used. On the other hand, for X-ray range a low-Z material such as Beryllium is usually the best choice.

In order to enable efficient propagation of the electromagnetic radiation in between the processing site of the article and the optical window(s) and to reduce the effects of the interactions of said radiation with the ambient medium (air), the apparatus is configured to create specific local conditions in the vicinity of the processing site, namely in the gap between the optical window and said site. By this, the interaction of the incident/returned beam with the atmosphere is reduced to an acceptable level, while keeping the article in ambient gases (air) environment.

The specific local conditions are conditions of reduced amount of ambient gases in the vicinity of a processing site (generally, in the region of interest), in the gap between the processing site and the optical window. This can be achieved by creating a substantially (quasi-) static state of VUV radiation non-absorbing environment in the vicinity of the processing site. Such static state is defined flow and/or pressure conditions of the VUV radiation non-absorbing environment. These may be conditions of specifically injected VUV non-absorbing gas(es) or those of ambient gas(es).

Figure 2A:
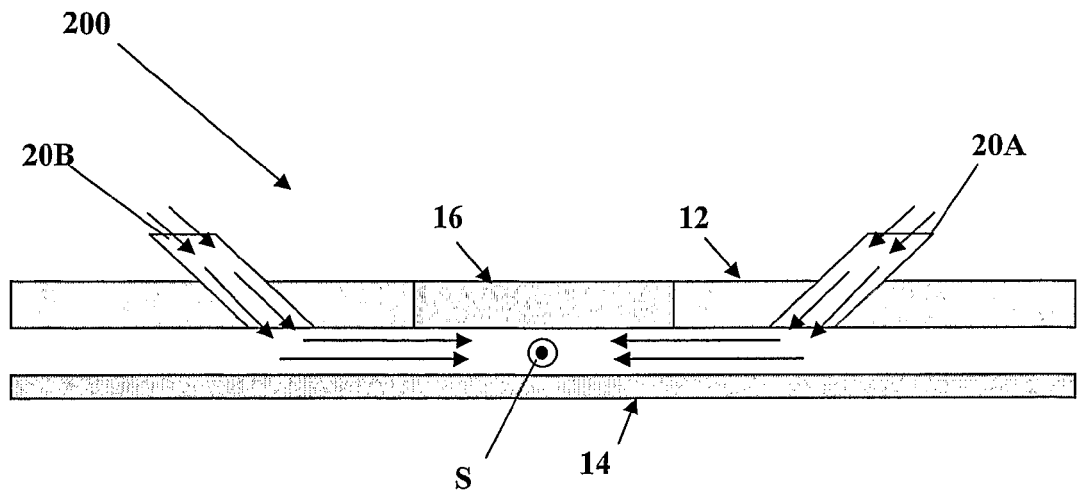
FIGS. 2A and 2B show an example of an apparatus of the present invention, where a zone of relatively high pressure is created in a gap between the optical window and the article by injection of inert gas.
Figure 2B:
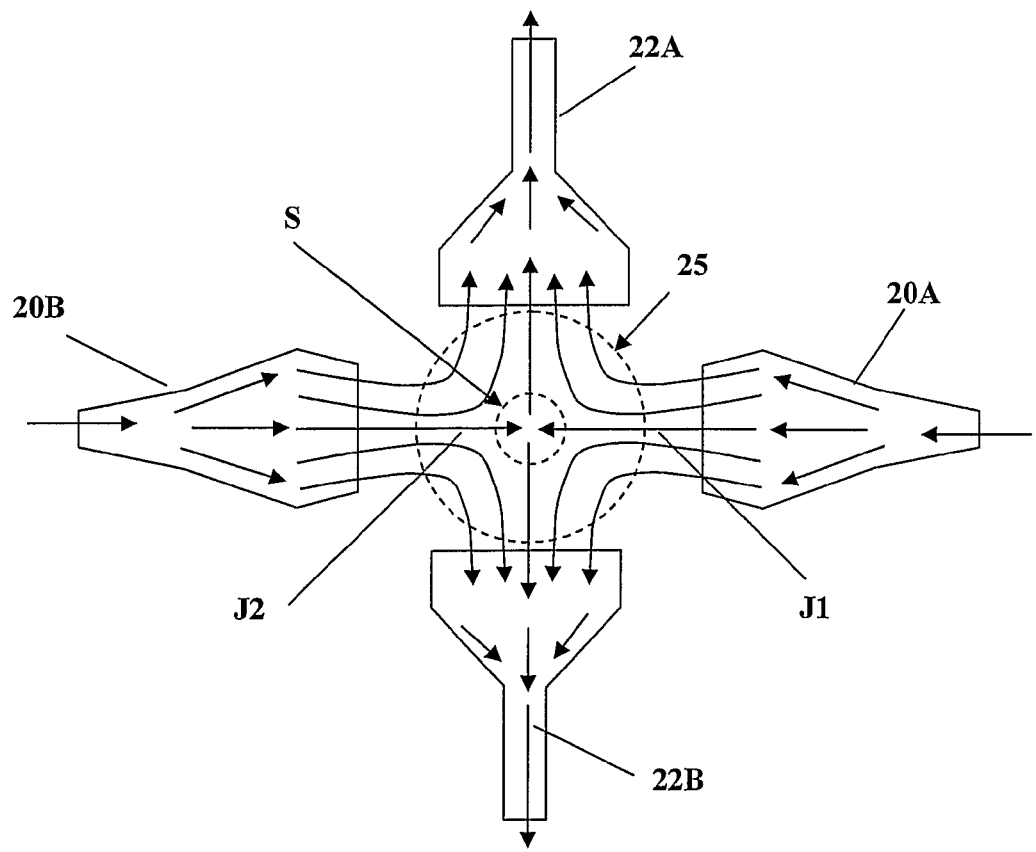

Reference is made to FIGS. 2A and 2B showing an example of the configuration and gas flow scheme in an apparatus 200 according to an embodiment of the invention.

The same reference numbers are used for identifying components common for all the examples. In this embodiment, the apparatus is configured to inject gas or gases non-absorbable with respect to radiation spectrum used (inert gases) into the gap region in the vicinity of the processing site. In order to create the substantially (quasi-) static state (flow, pressure conditions) of VUV radiation, non-absorbing environment the inert gas is supplied (injected) to the region of interest in multiple (generally at least two) jets flowing one towards another and interacting in the region of interest. Apparatus 200 includes a facet 12 (which may be a facet of a housing containing an optical system or defining a cavity for light propagation from and towards an external optical system), having a substantially planar surface 12A formed with an optical window 16. In this embodiment, the apparatus includes two gas inlet ports 20A and 20B arranged such that they supply gas jets J1, J2 flowing through the gap between the window(s) and the article in opposites directions and interfering with one another at the processing site region. It should be understood that there may be more than two interfering gas jets. Optionally the gas is discharged from the gap through two or more outlet ports 22A, 22B (generally exhaust systems) made in the facet 12. In the present example, the inlet and outlet ports are located symmetrically with respect to the optical window along two perpendicular axes. This configuration is based on the creation of a saddle-point of the gas flow at the interaction site, created by the collision of two inert gas jets. In this case there is a multitude of gas jets interfering at the processing site region and creating a zone of peak pressure at the vicinity of the processing site to thereby create a substantially quasi-static pressure point where turbulence is minimal thus preventing mixing of ambient gases with the injected inert gas preserving the purity of the inert gas at the interaction site. The formation of the saddle-point in the flow could be further enhanced by designing the injection nozzles in a way that will optimize such a flow profile, e.g. creating a converging flow at the exit from the nozzles, as well as the flow velocity.

Optionally, an effect of substantially static pressure point could be further enhanced during the optical processing of said site by shutting off the gas flow from the inlet ports 20A and 20B a predetermined time (practically, immediately) before the actual processing (measurement) is taken. Thus, inert gas is supplied to the gap region of interest (being in the vicinity of the processing site) in between measurement sessions, and a certain time before the measurement session the gas supply is halted and maintained such until the end of the measurement session. Since at the interaction volume the pressure of the injected gas was higher than the ambient pressure as long as the jets were on, the initial flow after closing the jets is expected to be outwards from the interaction volume, maintaining the purging gas as the dominant component in this volume and preventing air from flowing back in, for some additional time. Since the measurement time (or to be more exact illuminating/light collecting time) is typically short (of the order of 1 second or less), it could be expected that under suitable conditions the local purity of the purging gas will be maintained at a sufficient level while the measurement is being taken. It should be noted, although not specifically shown, that the apparatus comprises or is connectable to a control system (typically a computer system), which is configured and operable to manipulate the opening and closing of the jets' flow in accordance with the measurement sessions (i.e. controlling the amount and velocity of the gas jets).

It should be noted that creation of the (quasi)-static gas pressure conditions (e.g. saddle-point of the gas flow) in the vicinity of the wafer's edge might require the gas flow to be further modified. This is because in order to achieve the saddle point (i.e. a quasi static pressure zone), the forces exerted by the interacting flows (jets) on each other should be balanced at the saddle point, which condition might not exist at the wafer's edge.

Figure 2C:
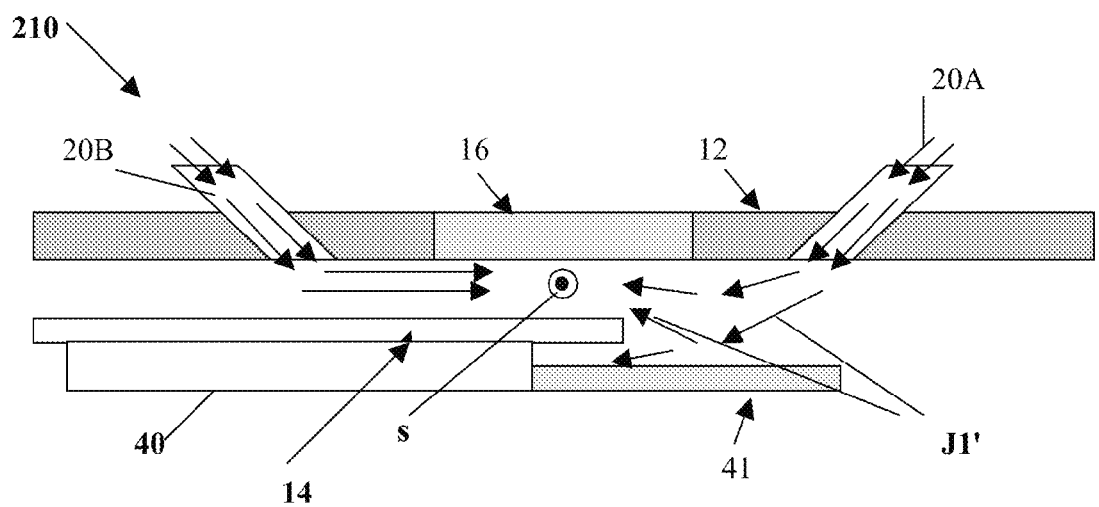
FIG. 2C shows another example of an apparatus of the present invention, where a zone of relatively high pressure is created in a gap between the optical window and the article by injection of inert gas.

Reference is made to FIG. 2C, showing an apparatus 210 generally similar to the above-described apparatus 200, but additionally configured to solve the above mentioned edge-related problem. The apparatus includes one or more assisting plates, one such plate 41 being shown in the present example. As shown in the figure, the wafer is typically located on a wafer chuck 40, supporting the wafer in its central region leaving the edge (periphery) region outside the chuck. The assisting (screen) plate 41 is located sufficiently close to the wafer below it, which in the present example is achieved by locating the plate 41 adjacent to the chuck, such that the surface of the plate 41 is substantially parallel to the wafer's surface. By this, the injected gas jets J1' which flow over the wafer's edge are redirected by the assisting plate, towards the gap between the wafer and the optical window, thus minimizing turbulent edge effects and resulting in the balanced pressure from all the jets at the interaction region (vicinity of the processing site). In certain embodiments of the present invention (not shown), the assisting plate is positioned adjacent to the edge of the wafer such that the surface of the wafer.

It should be noted that alternatively or additionally the flow parameters of inlet and/or outlet ports (pressure, flux) could be adjustable (by a control system). For example, a flow through the inlet port located aside the wafer may be increased in order to compensate at least partially for the lack of proper confinement in the vertical axis. It should be noted that optimal gas supply conditions could be modeled or defined before actual measurement during off-line mode (calibration, e.g. recipe creating) for all or at least some of the sites (for sites located in the wafer edge vicinity) and stored in the control unit memory, to be further used for controlling the gas conditions during the measurements.

It should also be noted that the angle or the shape of the gas inlet nozzle may be adjusted to improve the jet flow direction towards the region of interest in the gap.

Figure 3A:
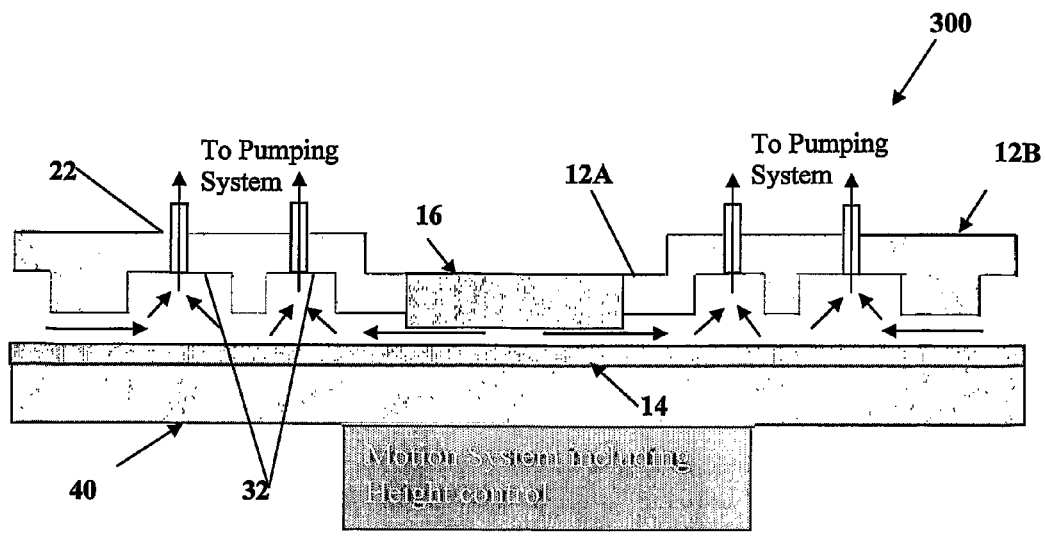
FIGS. 3A and 3B show another example of an apparatus of the present invention, where a zone of relatively low pressure is created in a gap between the optical window and the article.
Figure 3B:
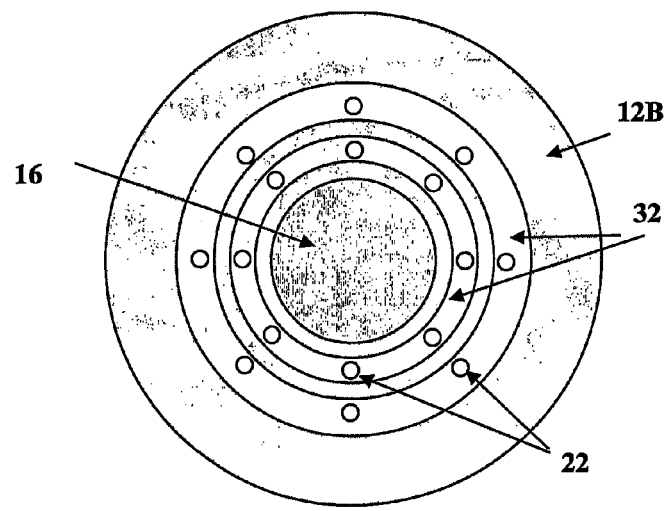

According to yet another embodiment of the invention, a zone of relatively low pressure constituting a zone of quasi-static pressure state) is created in the vicinity of the processing site, by using a pumping system. This is exemplified in FIGS. 3A and 3B showing an apparatus 300 in which a facet 12 has multiple gas outlet orifices connected to a pumping system (not shown). The orifices 22 are arranged in a spaced apart relationship around the optical window 16. In order to achieve a boundary condition of relatively uniform low pressure of the environmental gas (e.g. air), the surface portion 12B of the facet 12, surrounding the planar surface 12A, has one or more grooves 32 along which the orifices 22 are arranged. As a result, the pressure at a plane P defined by the planar surface 12A is relatively uniform along the groove. As shown in FIG. 3B, the orifices 22 are arranged along two spaced apart grooves 32 which are in the form of concentric rings around the optical window. A number of the concentric grooves, as well as a number of the orifices, is defined by a desired pressure gradient to be achieved in the radial direction. Thus, in this example, the quasi-static, low pressure, zone is created by using arrays of gas pumping outlets formed along one or more closed paths around the interaction spot. These paths (grooves in the specific implementation shown) create boundary conditions of low pressure around the interaction spot. Assuming no gas injection takes place inside the closed path, the pressure in the interaction spot will be equalized to that created on the path after sufficient time. Creating two or more such paths that are included in one another creates the effect of differential pumping and allows the system to reach a lower final pressure at the interaction spot.

In the present example, a wafer 14 under processing is shown as being located on a stage and supported thereon by a wafer chuck assembly 40. Also, in the present example the arrangement of multiple pumping ports (outlet orifices) and the grooves are similar to that used in several vacuum systems, e.g. vacuum chucks for holding wafers.

It should also be noted that it is desirable to make a distance between the optical window and the wafer as small as possible in order to minimize the total interaction of the optical beams with ambient gas or gasses (typically air) by controlling the total path length that the beams have to travel between the window and the processing site of the article. As exemplified in FIG. 3A, the facet 12 is configured such that the planar surface 12A carrying the optical window is brought closer to the wafer's plane than the surface portion of the facet in which pumping orifices are made (the so-called "system enclosure").

Figure 4:
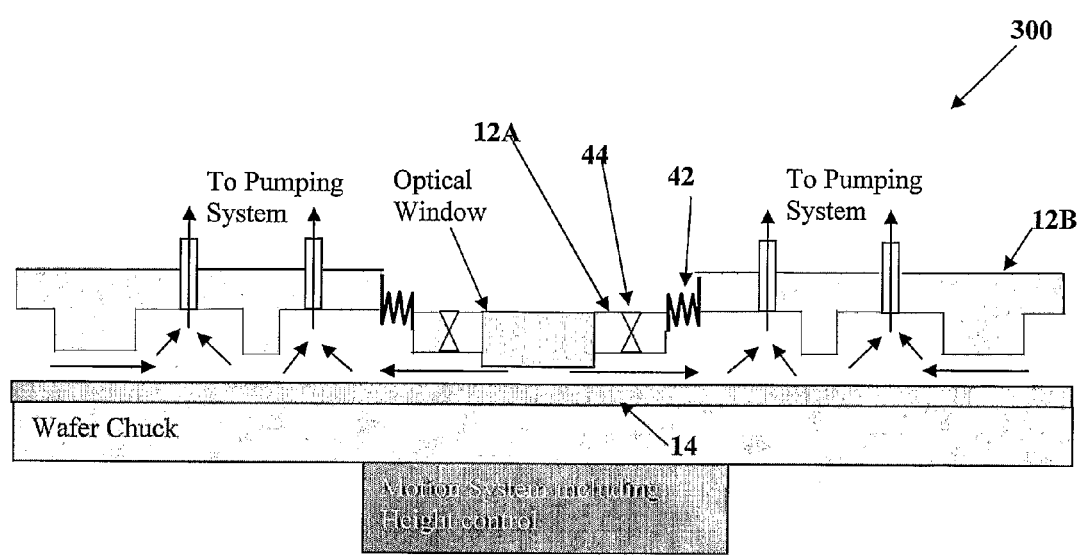
FIG. 4 is an example of the apparatus of the present invention based on the apparatus of FIGS. 3A-3B, and further configured to enable movement of the optical window with respect to the article.

Generally, a distance between the optical window and the article should preferably be adjustable to appropriately minimize this distance. In this connection, reference is made to FIGS. 4 and 5A-5B exemplifying apparatuses 300 and 100. Apparatus 300 of FIG. 4 is generally similar to that described above with reference to FIGS. 3A-3B, but in which the planar surface 12A carrying the optical window(s) 16 is residing on a separate part of the facet 12 being separated from the rest 12B of the facet by a flexible connection or "flexure" 42. The window(s) is/are thus free to move towards and away from the article along an axis perpendicular to the optical window.

In the example of FIG. 4, the movement of the optical window is controlled by a height control system 44 that can be mounted on the planar surface 12A. An example for an effective height control system that could be utilized in the apparatus of the invention may be a chuck equipped with gas nozzles such as described in U.S. Pat. No. 6,523,572. The planar surface portion 12A associated with the flexure 42 and the height control system 44 thus operates as a window chuck unit. The gas nozzles of the window chuck may be used for supplying an inert gas (in a controllable manner) into the gap between the optical window and the article, which will create forces that tend to bring a surface in front of them (i.e. the article) to an equilibrium distance from the nozzles. The equilibrium distance is stable to within microns. If the window chuck (planar surface portion 12A) is equipped with a sufficient number of such nozzles (elements 44) around the optical window 16, the optimal distance will be determined by the nozzles. Under flow conditions, the surface of the optical window could thus be brought to a very close distance from the wafer. Under no-flow conditions the system will be designed such that the flexure 42 is pulling the chuck away from the wafer 14, providing safe conditions for the wafer to move under the window.

It should be understood that a need for controlling the height is associated with the following: The pumping outlet orifices operate to create relatively low pressure zone below the optical window. When the optical window is mounted on a flexure, the reduction of pressure in the gap between the optical window and the article forces the optical window towards the article. Accordingly, the position of the optical window should be controlled. To facilitate maintaining the optical window at a stable position with respect to the article, inert gas may be supplied into the gap.

Figure 5A:
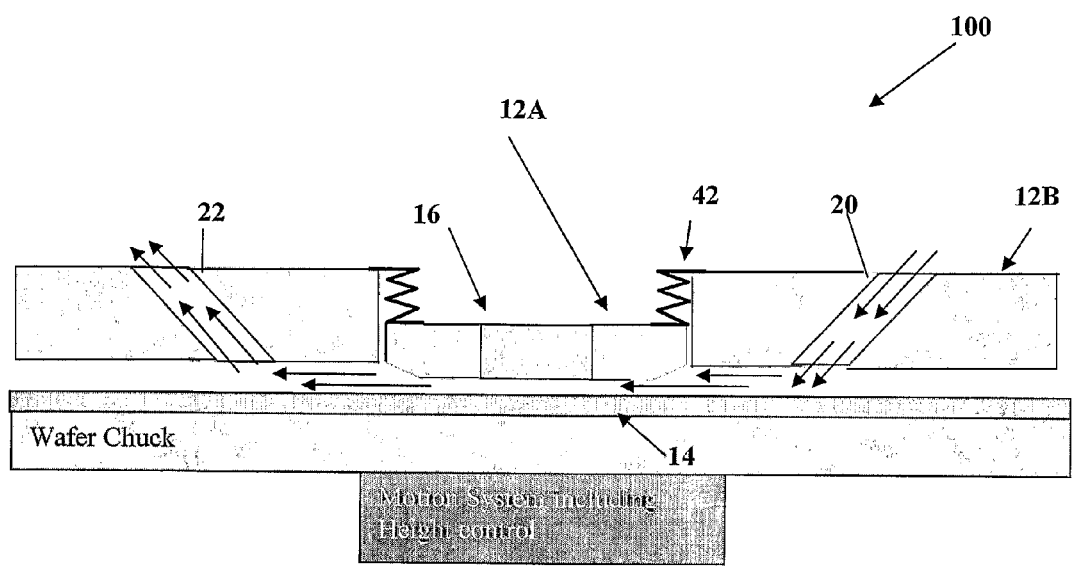
FIGS. 5A-5B show an example of the apparatus of the present invention configured to enable movement of the optical window with respect to the article.
Figure 5B:
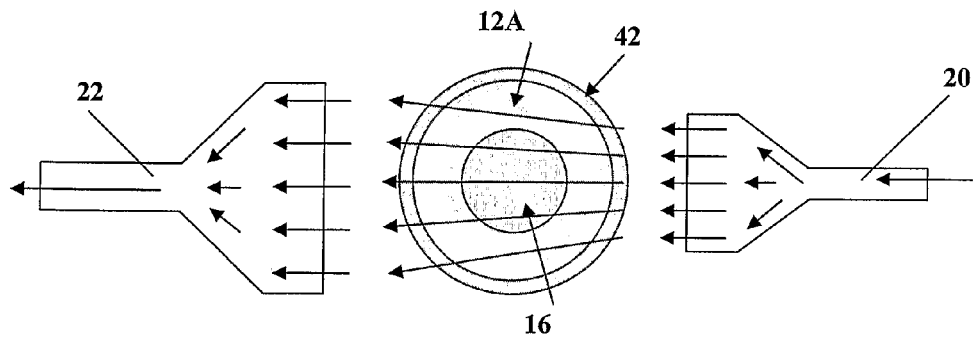

Reference is made to FIGS. 5A and 5B, where FIG. 5A shows schematically the configuration of a facet 12 having an optical window 16, and FIG. 5B shows the gas propagation scheme in the vicinity of the optical window (and thus in the vicinity of the processing site). In this example, the apparatus is configured to create a parallel flow of gas across the area in which the processing site is located. The facet 12 has a substantially planar surface 12A in which the optical window 16 is made. The surface 12A is held, by a flexure 42, in a position substantially parallel to the article's plane, i.e. to the surface of a support stage (e.g. wafer chuck) on which wafer 14 is located while being processed, thereby creating a gap between a wafer being processed and the surface 12A. The facet 12 is formed with one or more gas inlet ports (orifices), one such inlet port 20 being shown in the present example. The gas thus flows through the gap between the window(s) and the article and is then discharged from said gap. The facet 12 may or may not include one or more gas outlet (discharge) ports (orifices), one such outlet port 22 being shown in the present example. The inlet and outlet orifices may be located symmetrically with respect to the optical window.

The existence of a small gap between the window 16 and the wafer 14, and the substantially flat topography of the parallel surfaces of the wafer and the optical window 16 provides for appropriate conditions for laminar flow of gas within the gap. Thus a gas flow of an appropriate flow velocity evolves into a flow that is substantially laminar across the gap between the surface 12A and the wafer's plan (although some divergence of the flow is to be expected as shown in FIG. 5B). A laminar flow of the gas creates a Bernoulli effect according to which the static pressure is lowered in the presence of gas flow. Thus, the lower pressure, due to the flow under the window 16, will pull the window towards the article 14 (due to the difference in pressure between the two sides of the window), thereby reducing an optical path of the optical beam, thus reducing the interaction of optical beam with gases in the gap. In this embodiment, no control mechanism is required and the final distance between the optical window and the article can be set using the gas flow conditions (and possibly also the pressure in the optical system containing housing thereabove, as shown in FIGS. 1A and 1B).

In order to minimize the amount of turbulence or other disturbance an to provide stable laminar flow, it is also possible to use an exhaust system (constituted by outlet 22) that pulls gas away from the area around the interaction spot (processing site).

It should be further noted that the supplied gas(es), injected through the inlet orifice 20, may be ambient gas(es) (generally absorbing with respect to a spectrum being used). In this case the interaction of the optical beam with the gasses in the gap will be reduced mainly due to the shortening of the optical path within the gap (as described above) and due to the decrees in pressure due to the Bernoulli effect. However, providing for laminar flow within the gap and avoiding turbulent effects reduce the amount of ambient gases mixing with said injected gas, thus further reduction of the interactions of the optical beam with the gas(es) in the gap can be achieved by injecting an inert gas(es) (non-absorbing with respect to a spectrum being used). In this case the absorption of incident/returned light further decrease depending on the ability of the laminar flow of the injected gas to effectively repel the ambient air, which in turn is likely to be mostly dependent on the amount of turbulence.

Hence, the apparatus is designed to minimize such turbulence by designing suitable gas inlet port/orifice (nozzle) 20 (as well as the outlet one), for example to improve the lateral uniformity of the flow (the flow profile) before the gas entry of the interaction area, and/or to improve the design of the inlet port (its geometry) to provide a desired velocity of the gas flow through the optical window zone S, or the interaction site/spot.

The following are calculations aimed at evaluating the partial pressure of the ambient gasses of the atmosphere ($H_2O/O_2$) which is to be achieved in the vicinity of the processing site in order to verify sufficient transmission.

In this example, data provided in the U.S. Pat. No. 7,067,818 is used, according to which a concentration of 1 PPM ($P=10^{-6}$ bar ~1 mtorr) provides good transmission (>95%) for light down to a wavelength of 100 nm, over a path length of L=100 cm.

Transmission is exponential over the path length and absorption coefficient:

$$T = \exp(-K*L)$$

and the absorption coefficient, K, is expected to be linear with molecular concentration or partial pressure: $K=k*P$. Hence, $$T = \exp(-k*L*P).$$

Thus, in order to conserve the same transmission, one needs to conserve the product (L*P).

Assuming that the path length L is minimized to 1 mm, one can thus suffice with a partial $H_2O/O_2$ pressure of 1 mbar. Alternatively, reducing the path length to 100 microns, the pressure of 10 mbar can provide sufficient light transmission.

A number of embodiments have been described above. Nevertheless, it will be understood that various modifications may be made without departing from the spirit and scope of the disclosure. Accordingly, other embodiments are within the scope of the following claims.

The invention claimed is:

1. A method for use in optical processing of an article, the method comprising: maintaining an article under processing in ambient gas environment while creating local environmental conditions in a vicinity of a processing site of the article, said local conditions being characterized by substantially static state of environment, non-absorbable for predetermined electromagnetic radiation, in the vicinity of said processing site; said creating of the local environmental conditions comprising injecting into a free space gap in the vicinity of the processing site one or more gases non-absorbable with respect to said electromagnetic radiation used in the optical processing, and halting said injection a predetermined time before starting an optical processing session.

2. The method of claim 1, comprising providing at least two jets of said one or more gases flowing in opposite directions respectively and interfering in said gap in the vicinity of the processing site.

3. The method of claim 2, further comprising selective adjusting of the gas flows through said at least two jets thereby providing said substantially static state of environment, non-absorbable for predetermined electromagnetic radiation, in the vicinity of said processing site.

4. The method of claim 1, wherein said optical processing comprises optical measurements.

5. The method of claim 1, wherein said article is a semiconductor wafer.

6. The method of claim 1, wherein the condition of the substantially static state of environment comprises substantially static state of at least one of Nitrogen, Argon, and Helium.

7. The method of claim 1, wherein said predetermined electromagnetic radiation, non-absorbable by one or more gases comprises at least one of the following spectra: UV, DUV, VUV, and X-Ray.

8. An apparatus for carrying out the method of claim 1, the apparatus comprising:
- one or more optical windows for directing said electromagnetic radiation therethrough to illuminate said processing site and collecting radiation returned from the illuminated processing site thereby enabling optical processing of the article;
- two or more ports operable for gas inputting or discharging in the vicinity of the processing site on the article being processed; and
- a control unit configured and operable for providing selective adjustment of the gas inputting or discharging via said two or more ports by controlling the injection of one or more gases into a free space gap between said one or more optical windows and the article and halting said injection the predetermined time before starting a session of the optical processing, to thereby create said local environmental conditions in the vicinity of said processing site characterized by the substantially static state of environment non-absorbable for said electromagnetic radiation, thereby reducing amount of ambient gas in the vicinity of said processing site and enabling optical processing of the article while maintaining it in the ambient gas environment.

9. The apparatus of claim 8, wherein said substantially static state is defined by at least one of flow and pressure conditions of the environment non-absorbable for said electromagnetic radiation.

10. The apparatus of claim 8, configured and operable for feeding two or more jets of a gas, non-absorbable with respect to the electromagnetic radiation, in different directions towards the processing site such that said two or more jets interfere in the vicinity at said processing site.

11. The apparatus of claim 8, comprising a facet by which it faces the article being processed with a gap between said facet and the article, said facet comprising a substantially planar surface in which said one or more optical windows are made for transmitting and/or receiving therethrough electromagnetic radiation towards and/or from the processing site, said two or more ports comprising at least two orifices made in said facet for flowing gas therethrough into said gap between the optical window and the article, arrangement of the at least one optical window and said at least two gas orifices being such that a quasi-static gas pressure zone is formed in said gap, thereby enabling evacuation of the ambient gas surrounding the article from the vicinity of said processing site while keeping the article in the ambient gas environment.

12. The apparatus of claim 8, wherein said orifices comprise at least two gas inlets for injecting towards the processing site a gas non-absorbable with respect to said electromagnetic radiation.

13. The apparatus of claim 8 wherein the arrangement of the one or more optical windows and the at least two gas inlet ports is such that a saddle point of said gas flow is provided in the vicinity of the processing site, to thereby provide a zone of relatively high pressure at the saddle point.

14. The apparatus of claim 13, wherein the arrangement is such that the gas flow comprises gas jets flowing in opposite directions and interfering at said saddle point.

15. The apparatus of claim 8, wherein said gas ports are accommodated with respect to the one or more optical windows such as to substantially homogeneously input or discharge the gas from the vicinity of the processing site.

\* \* \* \* \*